(12) United States Patent
Ten Kate et al.

(10) Patent No.: US 11,911,187 B2
(45) Date of Patent: Feb. 27, 2024

(54) MONITORING A SUBJECT

(71) Applicant: KONINKLIJKE PHILIPS N.V., Eindhoven (NL)

(72) Inventors: Warner Rudolph Theophile Ten Kate, Waalre (NL); Mariana Nikolova-Simons, Eindhoven (NL); Enrique Antonio Gil Ponce, Eindhoven (NL); Josef Heribert Baldus, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 646 days.

(21) Appl. No.: 16/973,077

(22) PCT Filed: Jun. 11, 2019

(86) PCT No.: PCT/EP2019/065110
§ 371 (c)(1),
(2) Date: Dec. 8, 2020

(87) PCT Pub. No.: WO2019/238622
PCT Pub. Date: Dec. 19, 2019

(65) Prior Publication Data
US 2021/0244364 A1 Aug. 12, 2021

(30) Foreign Application Priority Data
Jun. 14, 2018 (EP) .................................. 18177791

(51) Int. Cl.
*A61B 5/11* (2006.01)
*A61B 5/00* (2006.01)
(Continued)

(52) U.S. Cl.
CPC .......... *A61B 5/7275* (2013.01); *A61B 5/1116* (2013.01); *A61B 5/1118* (2013.01);
(Continued)

(58) Field of Classification Search
None
See application file for complete search history.

(56) References Cited

U.S. PATENT DOCUMENTS

| 9,257,029 B1 | 2/2016 | Anderson |
| 9,536,052 B2 | 1/2017 | Amarasingham et al. |

(Continued)

FOREIGN PATENT DOCUMENTS

| WO | 2017106558 A1 | 6/2017 |
| WO | 2018145911 A1 | 8/2018 |

OTHER PUBLICATIONS

International Search Report and Written Opinion, International Application No. PCT/EP2019/065110, dated Sep. 11, 2019.
(Continued)

*Primary Examiner* — Ankit D Tejani (57) ABSTRACT

Presented are concepts for monitoring a health status of a subject. One such concept employs determining a trend in a health parameter of the subject based input data relating to a plurality of event occurrences for the subject. One or more irregularities are detected in the determined trend and health status of the subject is then determined based on the detected irregularities.

19 Claims, 4 Drawing Sheets

(51) Int. Cl.
  *G16H 50/30* (2018.01)
  *G16H 50/20* (2018.01)
  *A61B 5/16* (2006.01)

(52) U.S. Cl.
  CPC ............ *A61B 5/162* (2013.01); *A61B 5/4806* (2013.01); *A61B 5/7267* (2013.01); *A61B 5/7475* (2013.01); *G16H 50/20* (2018.01); *G16H 50/30* (2018.01); *A61B 2562/0219* (2013.01); *A61B 2562/0247* (2013.01)

(56) References Cited

U.S. PATENT DOCUMENTS

| | | |
|---|---|---|
| 10,854,063 B2 | 12/2020 | Ten Kate et al. |
| 2008/0084296 A1 | 4/2008 | Kutzik et al. |
| 2014/0052465 A1 | 2/2014 | Madan et al. |
| 2019/0156645 A1* | 5/2019 | Bolduc .............. G08B 21/0461 |

OTHER PUBLICATIONS

Vermeiren, D., "Detecting human motion: Introducing step, fall and ADL algorithms", Oct. 5, 2009.
Pirsiavash, H. et al., "Detecting Activities of Daily Living in First-Person Camera Views", University of California, 2012.

* cited by examiner

MONITORING A SUBJECT

CROSS-REFERENCE TO PRIOR APPLICATIONS

This application is the U.S. National Phase application under 35 U.S.C. § 371 of International Application No. PCT/EP2019/065110, filed on 11 Jun. 2019, which claims the benefit of European Patent Application No. 18177791.3, filed on 14 Jun. 2018. These applications are hereby incorporated by reference herein.

FIELD OF THE INVENTION

This invention relates to monitoring a subject (such as a subject or a patient) and more particularly to monitoring a health status of a subject.

BACKGROUND OF THE INVENTION

Functional assessment or monitoring of a subject's health status, physical abilities, mental abilities, or recuperation after injury, hospitalization and treatment is of primary concern in most branches of medicine, including geriatrics, rehabilitation and physical therapy, neurology and orthopaedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a subject at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they live independently in their own home or within familiar surroundings. For example, one such known system for detecting activities of daily living of a subject system comprises three main components: (i) a sensor system that collects information about the subject's activities and behaviours; (ii) an intelligence (or information processing) system that interprets the sensor signals for determination of ADL behaviour; and (iii) a user interface system that enables care givers to inspect the interpreted (processed) information. The intelligence system typically makes use of computational techniques known in the art as artificial intelligence. The system may be supported by conventional technologies for data collection, transmission, and storage.

In practice, however, a major difficulty is encountered by the wide range of variations that can happen in actual care cases. Since there are so many possible circumstances, situations and contexts that can occur in daily life, it is common to employ numerous sensors in an attempt to capture enough information about a subject's activities to enable identification of specific activities. This, however, typically increases costs and requires a monitored subject to accept sensors throughout their home (which may be unacceptable or feel like an intrusion into privacy).

The ever-increasing complexity in striving to cover all possible contexts and situations requires more elaborate and detailed information to be collected, processed, interpreted and/or communicated. Accuracy, or the amount of relevant information generated, may also be reduced by trying to cater for a large number of alternate situations. For example, although many situations may not be relevant to a monitored subject, these irrelevant situations may still be accounted for and selected by the system, thus providing erroneous responses.

Also, a monitored subject's physical and/or mental abilities may vary (e.g. decline or reduce) over time. As a result, it can be difficult to determine when some form of care activity (such as assistance, help or supervision) may be needed.

SUMMARY OF THE INVENTION

The invention aims to at least partly fulfil the aforementioned needs. To this end, the invention provides systems and methods as defined in the independent claims. The dependent claims provide advantageous embodiments.

There is provided a system for monitoring a health status of a subject, wherein the system comprises: a signal interface adapted to receive input data relating to a plurality of event occurrences for the subject, the input data comprising, for each event occurrence, information representative of at least one of: activity of the subject; and care activity provided to the subject; a processing unit adapted to determine a trend in a health parameter of the subject based on the input data; a trend analysis unit adapted to detect one or more irregularities in the determined trend; and a monitor unit adapted to classify each of the one or more irregularities as at least one of: an outlier to the trend; and a changepoint in the trend and to determine a health status of the subject based on the irregularity classification of each of the one or more irregularities, wherein the health status of the subject is representative of at least one of: a risk of an adverse event occurrence; and a time until care activity requirements change, and wherein the monitor unit is adapted to determine, based on the irregularity classification of each of the one or more irregularities, at least one of: a value of risk of an adverse event occurrence; and a value of time until care activity requirements change.

Proposed is the concept for monitoring a physical or mental health status of a subject by identifying irregularities in a trend in a health parameter of the subject. By using irregularities or anomalies in a trend, changes or irregularities in a subject's behaviour may be identified and analysed to identify if an accident has occurred or substantive change in health is happening. For example, by detecting a consistent change or pattern in a trend of a health parameter, an alteration in a subject's physical or mental health (beyond which may normally be expected due to aging or disease progression) may be inferred. From this, current and/or future care/help/assistance requirements may be determined.

Thus, there is proposed the concept of determining a trend in a subject's health parameter and determining a health status of the subject based on irregularities in the trend. Furthermore, an alert may be provided to a care provider to raise awareness of the irregularities. If a detected irregularity is accidental, an alert may be provided so as to warn about the possibility of an increased risk for an adverse event. If a detected irregularity is structural (e.g. linked to a substantive or fundamental change in the trend), a time until a next level of care (i.e. a change in care requirements) may be determined and an indicator provided to notify a user about this change.

Embodiments may thus enable care activities/services to be provided to the monitored subject more effectively and/or more efficiently. For instance, accurate determination of a health status of the subject may provide a better understanding of the care requirements for the subject. Further, a forecast of the healthcare needs may be provided based on the determined health status (e.g. a prediction that a next level of care will be needed may be provided in a timely manner). An expected time until care requirements will alter (e.g. increase to a next level of care) may also be estimated by embodiments. Proposed embodiments may therefore enable improved (e.g. more accurate) forecasting of a subject's health status and/or care requirements.

Embodiments may therefore enable the monitoring of a subject's health status by detecting and analysing irregularities or anomalies in a trend of a health parameter of the subject. A trend of a health parameter may be determined from input data relating to a plurality of event occurrences for the subject. For example, a health parameter of a subject may comprise: speed; strength; reaction speed; mobility; sleeping pattern (e.g. duration, sleep begin and wake up time, number of bed leaves during night; level of movements while sleeping, etc.); number of toilet visits during day; duration of toilet visits; duration in bathroom; activity level; eating/drinking behaviour or pattern; movement measure (e.g. sitting all day, or occasionally traversing, or traversing in abnormal patterns; sit-to-stand behaviour; time on feet; duration of walking/ambulating; regularity of walking; or walking speed. Embodiments may derive values of such health parameters from information representative of: activity of the subject; or care activity provided to the subject that is provided for detected event occurrences.

An activity may comprise an Activity of Daily Living (ADL) that concerns a basic activity a subject may execute on a regular basis. Examples of such activities of daily living are drinking/eating; cooking; medicating; sleeping; toileting; bathing; washing, any kind of exercising such as walking, leisure activities such as reading or TV watching and many more etc. Thus, the invention may provide a way to monitor a health status of a subject based on one or more ADLs (such as cooking, eating, exercising, opening doors, etc.) in a simple and easy to implement manner.

Embodiments may be adapted to distinguish between different types of anomalies. Such different types of anomalies may impact the health status of the subject differently, and so classifying the irregularities may assist (e.g. simplify) an assessment of the health status of a subject based on the irregularities.

A health status of the subject may be described using one or more parameters for defining a state of physical or mental characteristics of a subject. Thus, reference to a subject's health status should not be taken to refer to an entire, overall or complete description of a subject's health (which may for example require a large number of health parameters and descriptors to be defined). Instead, reference to a subject's health status should be understood to refer to an indication of an aspect of the subject's health or well-being and which is described using a limited/restricted number of parameters (preferably fewer than ten in total, more preferably fewer than five in total, and even more preferably only one or two in total).

For example, the health status of the subject may be representative of: a risk of an adverse event occurrence; and a time until care activity requirements change.

Also, the monitor unit may be adapted to increase a value of risk of an adverse event occurrence if an irregularity is classified as an outlier to the trend, and to decrease a value of time until care activity requirements change if an irregularity is classified as changepoint in the trend. An outlier to the trend may be associated with event occurrences, e.g., frequent toilet visits, large number of calls in a week, etc., and may be identified when a detected value deviates more than p-times the standard deviation (e.g. where p=2 or some other customizable value). A changepoint in the trend may be indicative of a point where the trend itself is modified (e.g., faster decline in walking speed or activity level), and may be identified when the last few data points or values have a better fit (e.g. regression) to a new trend that is different from the previously determined. Changepoint detection is well known in the art and numerous different techniques for identifying changepoints are described in widely-available literature.

By way of example, in some embodiments, the trend analysis unit may be adapted to identify whether there are of one or more irregularities in the determined trend based on at least one of: a comparison of the determined trend with a threshold value; a comparison of information of an event occurrence with an average value; and a comparison of the determined trend with a predetermined trend. Thus, to detect an irregularity, the monitor unit may undertake a comparison of the determined trend with a threshold value. For example, the monitor unit may employ a data processing unit that compares the determined trend with a threshold value. The threshold may be preprogramed and fixed, but it may be preferable to enable the threshold value to be set by a user preference. Also the threshold value may relate to a future value, and the trend may be extrapolated for comparison of an extrapolated value with the future threshold value. This may identify when a threshold value may be exceeded in the future, for example.

Also, the threshold value may be determined based on at least one of: one or more previously obtained values of a property of at least one of: an activity of the subject; and care activity provided to the subject; and one or more previously determined changes in values of a property of at least one of: an activity of the subject; and care activity provided to the subject. The threshold may thus be based on previously detected values and/or previously determined event occurrences for the subject. In other words, the threshold may be defined by taking account of a history of detected values and/or a history of events so that it can be used to identify outlying values or anomalies.

In some embodiments, the system may further comprise: a prediction unit adapted to calculate, based on the determined health status of the subject, an estimated future time at which supervision, care or intervention will be required by the subject. This may provide the advantage of identifying a future time when care requirements of the subject will increase, thus enable more efficient allocation of (current and future) care resources.

The prediction unit may be further adapted to calculate an estimated future value of a property of at least one of: activity of the subject; and care activity provided to the subject based on the determined trend and the determined health status of the subject. Accurate determination of a subject's physical ability and/or care needs may therefore be facilitated by proposed embodiments. This may help to provide cost savings (e.g. in a health care system) by timely enabling intervention. Embodiments may therefore be useful for identifying future requirements of a monitored subject, and this may be achieved via extrapolation of a trend and/or health status determined by a proposed embodiment.

Information representative of at least one of: activity of the subject; and care activity provided to the subject may comprise information relating to a detected value of a property of at least one of: the subject; and an object manipulated by the subject. Such information may be obtained, for example, using simple and conventional sensors that are already widely employed in monitoring systems. Embodiments may therefore be simple and cheap to implement.

The property may comprise at least one of: a velocity (e.g. translational and/or rotational) or speed of movement of the subject or the object; a measure (such as magnitude, speed/rate of change, average, etc.) of force (or derivatives thereof) applied by the subject to the object; a distance travelled by the object or a body part of the subject; a rate of acceleration of the object or body part of the subject; a reaction time of the subject; a measure of posture of the subject; and a bodyweight of the subject. By detecting values of a property of a subject and/or an object that the subject interacts with, a trend in the detected values over time may be identified and, from such a trend, a physical or mental capability of a subject may be monitored.

For example, a trend of declining/decreasing velocity or speed of movement of the subject (as detected directly, using cameras, for example, or inferred using an accelerometer affixed to the subject, or as detected indirectly using an accelerometer integrated into an object that is moved by the subject) may be used to identify and monitor the subject's physical strength or speed. By way of another example, a trend of increasing reaction time of the subject may be determined based on information from a timing device that detects an amount of elapsed time between a prompt or signal and a response from the subject.

Embodiments may be further adapted to store the input data in a database adapted to store historical data relating to one or more previously detected values of the property. Previously determined values of a property of the subject or an object may therefore be stored, in a historical database for example, and then used in subsequent calculations. Furthermore, currently detected values may be used to re-calculate or refine a previously determined trend.

Embodiments may comprise a user input interface adapted to receive a user input for defining or modifying input data. This has the advantage of enabling a user to manually provide and/or edit information, which may be useful in ensuring accurate and/or relevant information is employed for determinations.

The monitor unit may be further adapted to generate a control signal for modifying a graphical element based on the determined health status of the subject. Further, the system may further comprise a display system adapted to display the graphical element in accordance with the control signal generated by the monitor unit. In this way, a user (such as a care giver) may have an appropriately arranged display system that can receive and display information about the health status of the subject, and that subject may be remotely located from the user. Embodiments may therefore enable a user to remotely monitor a subject (such a patient or elderly subject) using a portable display device, such as a laptop, tablet computer, mobile phone, PDA, etc.

It will be appreciated that all or part of the monitor unit may comprise one or more data processing units. For example, the monitor unit may be implemented using a single processor which is adapted to undertake data processing in order to determine a health status of a subject.

The monitor unit may be remotely located from one or more sensors that provide the input data, and a signal representative of the input data may be communicated to the processing unit or the monitor unit via a communication link.

The system may further comprise: a server device comprising the monitor unit; and a client device comprising the signal interface. Dedicated data processing means may therefore be employed for the purpose of determining a health status of the subject, thus reducing processing requirements or capabilities of other components or devices of the system.

The system may further comprise a client device, wherein the client device comprises the monitor unit and a display system. In other words, a user (such as a care giver) may have an appropriately arranged client device (such as a laptop, tablet computer, mobile phone, PDA, etc.) which processes received data in order to determine a health status of the subject.

Thus, processing may be hosted at a different location from where the sensing or data provision happens. For example, for reasons of power efficiency (e.g. to improve battery lifetime) it might be advantageous to execute only part of the processing at a sensor location, thereby reducing associated costs, processing power, transmission requirements, etc.

Thus, it will be understood that processing capabilities may therefore be distributed throughout the system in different ways according to predetermined constraints and/or availability of processing resources.

Embodiments may comprise a sensor arrangement/system positioned in a strategic position so that it detects the appropriate values of activity without the subject needing to intentionally or consciously activate/operate the sensor. In this way, a subject may only need to undertake their normal activities. Such strategic positioning may ensure that a value of a property of the subject or environment can be automatically and accurately obtained, and this may not require the subject to remember to undertake any special or additional activities in order for a value to be detected by the sensor. This may remove the risk of the subject forgetting to activate a sensor (e.g. by pressing a button), for example.

There exist many sensors that can be employed by a monitoring system according to an embodiment. Typical sensors include PIR (Passive Infra-Red; measure movement and presence), OC (open-close; measure state of doors, in particular front doors, windows, and cupboards, including refrigerators), power sensors (measure current consumption of appliances, such as microwave, water cookers, TV, etc.); and pressure sensors or mats (measure occupancy of user sitting in chair, lying in bed, standing on door mat in front of front door, being at toilet, etc.). Many others exist and are conceivable, such as sensors to signal light switch state, or sensors that measure environmental conditions such as humidity, $CO_2$ level (or CO and smoke), Particulate Matter level, etc. A further range of sensors are those based on physical quantities, such as accelerometers, magnetometers, gyroscopes, and air pressure sensors. Accelerometers, for example, can also measure state of doors and their open-close movements or measure speed or velocity of movement of a subject or an object moved by the subject. Yet another range of sensors consists of microphones and cameras (including infra-red, or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home system.

Although the sensor(s) may be mounted in the monitoring environment (e.g. the subject's home), they may also be attached to user utilities (such as a keyring) or put in clothes, in a pocket or bag, or as insole or undergarment, etc. They may also be fabricated to be worn explicitly like a wristwatch or pendant. Further, the sensors may communicate their output signals via a wired or wireless connection, or a combination thereof. Accordingly, in an embodiment, a sensor may be adapted to be coupled to the subject or the object. The object may for example comprise an item of furniture (such as a fridge, cupboard, wardrobe, seat, door, white good, etc.) adapted to be used in the execution of an ADL.

Employed sensors may also be adapted to undertake primary processing of the detected values, such a signal filtering, sampling, conditioning, etc., so as to reduce required transmission bandwidth and/or transmission duration for example. Alternatively, the sensors can send raw data.

Non-intrusive monitoring may therefore be realized with relatively simple sensors that provide data on specific ambient conditions or properties/parameters of an object, an environment (such as temperature or humidity for example), or properties of the subject (such as movement, weight, speed, weight, and/or distance travelled for example). Such sensors for measuring ambient condition or properties/parameters of the object or environment may be simple, small and/or cheap. Also, the movement of the subject may be detected with, for example, a Passive Infrared (PIR) sensor which is a cheap component. Movement sensors may be used to switch on lighting and people are therefore typically familiar with their usage.

Thus, systems of the invention may employ conventional sensors and/or existing sensor arrangements. Also, embodiments may employ sensors that are considered to be non-intrusive and more easily accepted by the monitored subject. Yet, with the data provided by these sensors, activities may be determined and provide information on the subject being monitored.

Such sensors may be employed by, or in conjunction with, embodiments so as to increase the number and/or accuracy of monitored activities. They may also be used to confirm or qualify readings taken by a sensor, so that spurious or unintentional measurements are avoided. For example, signals from a location sensor worn by the monitored subject may be used to confirm if weight readings taken by a weight sensing system are indeed attributable to the monitored subject or some other subject or animal (such as their pet), for example.

According to another aspect of the invention, there is provided a method for monitoring a subject, wherein the method comprises: receiving, at a signal interface of a system for monitoring a health status of the subject, input data relating to a plurality of event occurrences for the subject, the input data comprising, for each event occurrence, information representative of at least one of: activity of the subject; and care activity provided to the subject; determining, with a processing unit of the system, a trend in a health parameter of the subject based on the input data; detecting, with a trend analysis unit of the system, one or more irregularities in the determined trend; classifying, with a monitor unit of the system, each of the one or more irregularities as at least one of: an outlier to the trend; and a changepoint in the trend; and determining, with the monitor unit of the system, a health status of the subject based on the irregularity classification of each of the one or more irregularities, wherein the health status of the subject is representative of at least one of: a risk of an adverse event occurrence; and a time until care activity requirements change, and wherein determining a health status of the subject comprises: determining, based on the irregularity classification of each of the one or more irregularities, at least one of: a value of risk of an adverse event occurrence; and a value of time until care activity requirements change.

There is also provided a computer program product for monitoring a subject, wherein the computer program product comprises computer-readable program code executable to perform a method according to an embodiment on a system according to a proposed embodiment.

A computer system may be provided which comprises: a computer program product according to an embodiment; and one or more processors adapted to perform a method according to an embodiment by execution of the computer-readable program code of said computer program product.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying schematic drawings, in which.

DETAILED DESCRIPTION OF THE EMBODIMENTS

Proposed is a concept for monitoring a health status of a subject (such as a patient or subject) based on irregularities identified in a trend of a health parameter of the subject. This may be useful for the purpose of unobtrusively monitoring the well-being of the subject for example. Such subjects may, for instance, include a disabled subject, an elderly subject, an injured subject, a medical patient, etc. Elderly subjects can mean subjects above 65 years, above 70, or above 80 years old.

Illustrative embodiments may be utilized in many different types of monitoring environments, such as a hospital, ward, care home, subject's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

In general, to be able to observe or identify trends in "normal" daily behavior of a subject one may monitor ADLs of a subject. From determined trends, one may also spot unexpected activities, anomalies, irregularities or deviations from expected values or patterns. The type of anomaly or irregularity can be different per case.

A large class of physical or mental capabilities can relate to an ADL routine of the subject. For example, a physical capability may be inferred from the speed by which a subject opens/closes a door (or a cupboard, wardrobe, fridge, microwave, or other furnishings) or a drawer and/or the force applied to the door or drawer during the opening/closing process.

Embodiments of the present invention are directed toward enabling information about a health status (e.g. physical capability) of a subject to be obtained and potentially monitored. Such information may therefore be useful for monitoring the health or well-being of a subject. It may also be useful for predicting when care requirements of the subject may change (e.g. increase) so as to require different care resource or facilities.

Embodiments employ the concept of determining a trend in a health parameter of the subject from information representative of activity of the subject and/or care activity provided to the subject. In other words, determination of a trend in a health parameter of a subject may be based on current and previously detected properties of the subject's activity or care activity provided to the subject. Such properties may relate to the strength, speed, reaction time, mobility, coordination of the subject, and may be detected by one or more sensors that detect a force exerted by the subject, a speed of a body part of the subject or the object, angular velocity of a body part of the subject or the object, the weight of the subject, and the like, and this may be undertaken in relation to particular ADLs.

A trend in a physical or mental capability of a subject may therefore be determined using a single sensor (e.g. an accelerometer) installed at a single location (e.g. a door or drawer), thus reducing the burden, cost and/or complexity of a system according to an embodiment. It may also help to ensure that anomalies are accurately detected, thus improving the accuracy of monitoring results. Such a proposed concept for monitoring a physical or mental capability of a subject may therefore be employed in a system for monitoring ADLs of a subject within an environment.

Physical activities of a subject care activities provided to the subject may be detected or inferred from sensor output signals and there already exist systems and methods for such detection or inference. Accordingly, the proposed concepts may be used in conjunction with existing ADL detection or monitoring systems/methods. For example, Dries Vermeiren et al describe a system based on 2 tri-axial accelerometers to detect the ADLs of a patient in a paper entitled "Detecting Human Motion: Introducing Step, Fall and ADL algorithms". Also, H Pirsiavas et al describe algorithms for detecting ADLs in first-subject camera views in paper entitled "Detecting activities of daily living in first-subject camera views" (CVPR, 2012). Because many such ADL detection or monitoring methods/systems are known and any one or more of these may be employed, detailed description of such methods/systems is omitted from this description.

Embodiments also employ the concept that a health status of a subject may be determined based on one or more irregularities identified in the determined trend. By using irregularities in a trend, changes or alterations in a subject's behaviour may be identified and analysed to determine if an accidental or substantive change in the health status has occurred. For example, by detecting a changepoint in a trend of a health parameter, an alteration in a subject's physical or mental health (beyond that normally be expected due to aging or disease progression) may be inferred. From this, a change in current and/or future care requirements may be determined. By way of further example, if a detected irregularity is accidental, an alert may be provided so as to warn about the possibility of an increased risk for an adverse event.

Figure 1:
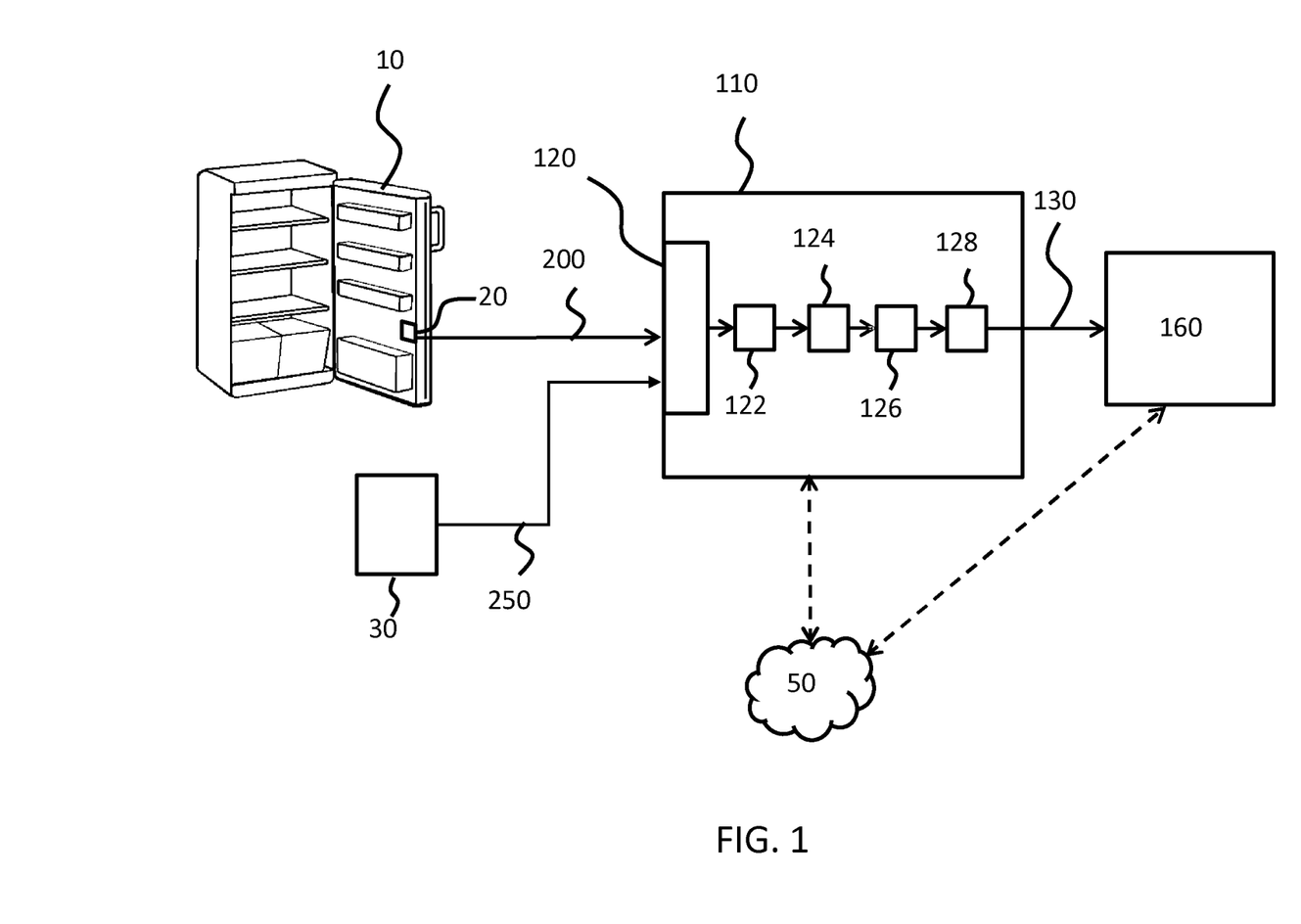
FIG. 1 is a simplified block diagram of a system adapted to monitor a health status of a subject according to an embodiment.

FIG. 1 shows an embodiment of a subject monitoring system according to the invention comprising a fridge door 10 and a motion sensor 20 adapted to detect a velocity of the fridge door 10 which results from the subject's usage (e.g. opening or closing) of the fridge door 10.

Here, the motion sensor 20 is integrated into the fridge door 10 so that it moves with the fridge door 10. For example, the motion sensor 20 may comprise an accelerometer, magnetometer, and gyroscope. A gyroscope is of particular interest when the fridge door 10 is a rotating one (i.e. hinged at one side to that it is rotated about a vertical axis when opened/closed) like that shown in FIG. 1. Since a gyroscope measures rotation velocity, it can be mounted at any spot of the fridge door 10. For example, it can be mounted close to the hinge or rotation axis so that is hidden from sight, or it can be mounted far from the hinge (e.g. close to the handle of the fridge door shown in FIG. 1) so that it can be accessed easily (for repair or replacement for example).

In this way, a subject need only undertake their normal activities when using the fridge and may not even be aware that they are operating the motion sensor and being monitored. Such positioning (integrated into the fridge door 10, for example) may ensure that a property of the subject or the fridge door 10 (such as: a velocity or speed of movement of the door 10; a magnitude of force applied by the subject to the door 10; a distance travelled by the door 10; a rate of acceleration of the door 10; the duration of opening/closing of the door; the impulse (integrated force/acceleration); or the (peak) power (force/acceleration time velocity) exercised during open and/or close, for example) can be automatically and accurately obtained for each single usage (e.g. opening or closing) of the fridge (e.g. every time the subject accesses the contents of the fridge) without requiring the subject to remember to undertake any special or additional activities in order for a property of the subject or the fridge door 10 to be detected. For example, it can remove the need for a subject to perform a specific additional action (e.g. pressing a button) in order to activate the motion sensor 20.

The motion sensor 20 comprises a motion sensing arrangement that is adapted to determine a velocity of movement of the fridge door 10, a distance travelled by the fridge door 10, and a rate of acceleration of the fridge door 10, when the fridge door 10 is opened. The motion sensor 20 may obtain numerous measurements before, during and after the subject opens or closes the fridge door.

The motion sensor 20 is adapted to output sensor output signals 200 which are representative of the detected value(s) of the fridge door 10 during an opening or closing event occurrence. Of course, many more sensors may be employed so as to provide signals indicative of detected values of properties of the subject and/or the fridge door. For example, the magnitude of a pulling or pushing force applied by the subject to the fridge door may be detected using one or more pressure sensors. Such additional signals may be useful for identifying which of the sensor output signals 200 are indicative of a property of the subject or the fridge door 10. They may also be used to confirm or qualify values detected by the motion sensor 20, so that spurious or unintentional measurements are avoided. For example, signals from a location sensor worn by the monitored subject may be used to confirm if values detected by the motion sensor 20 are indeed attributable to the monitored subject operating the fridge door 10, for example.

The system also comprises a care input module 30 adapted to receive user inputs indicative of care activity provided to the subject. Here, the care input module 30 comprises a tablet computer that is carried by the subject's carer or medial assistant and includes an application for facilitating the provision of information regarding care activities provided to the subject. In this way, the system provides for the input of data comprising information representative of care activity provided to the subject. The subject's carer or medial assistant need only undertake their normal care activities when caring for the subject and then use the application to provide information describing the care activities.

The care input module 30 is adapted to output care signals 250 which are representative of the care activity provided to the subject.

The motion sensor 20 and care input module 30 both communicate their output signals 200,250 via a respective wired or wireless connection. By way of example, the wireless connection may comprise a short-to-medium-range communication link. For the avoidance of doubt, short-to-medium-range communication link may be taken to mean a short-range or medium-range communication link having a range of up to around 100 meters. In short-range communication links designed for very short communication distances, signals typically travel from a few centimetres to several metres, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), Near Field Communication (NFC), RFID, 6LoWPAN, UWB, Wireless HART, Wireless HD, Wireless USB, ZigBee. Examples of medium-range communication links include Wi-Fi, ISM Band, Z-Wave. Here, the output signals are not encrypted for communication via the wired or wireless connection in a secured manner. However, it will be appreciated that, in other embodiment, one or more encryption techniques and/or one or more secure communication links may be employed for the communication of signals in the system.

The system further comprises a system 110 for monitoring a health status of a subject according to an embodiment. The system comprises a signal interface 120 adapted to receive the sensor output signals 200 and the care signals 250. The signal interface 120 provide the received signals 200,250 to a processing unit 122 of the system 110.

The processing unit 122 adapted to determine a trend in a health parameter of the subject based on the received signals 200,250. For this purpose, the processing unit 122 may communicate with one or more data processing resources available in the internet or "cloud" 50. Such data processing resources may undertake part or all of the processing required to infer or determine a trend in a health parameter of the subject based on the received signals 200, 250. Thus, the embodiment may employ distributed processing principles.

The system 110 also comprises a trend analysis unit 124 that is adapted to detect one or more irregularities in the determined trend. Again, for this purpose, the trend analysis unit 124 may communicate with one or more data processing resources available in the internet or "cloud" 50. Such data processing resources may undertake part or all of the processing required to detect one or more irregularities in the determined trend.

Here, the trend analysis unit 124 is adapted to identify whether there are one or more irregularities in the trend based on at least one of: a comparison of the determined trend with a threshold value; a comparison of information of an event occurrence with an average value; and a comparison of the determined trend with a predetermined trend. The threshold value is a predetermined value and is calculated previously obtained values of a property of an activity of the subject and care activity provided to the subject.

The trend analysis unit 124 is adapted to provide information about the detected irregularities to a monitor unit 126 of the system 110. The monitor unit 126 is adapted to determine a health status of the subject based on the detected irregularities. Again, for this purpose, the monitor unit 126 may communicate with one or more data processing resources available in the internet or "cloud" 50. Such data processing resources may undertake part or all of the processing required to determine a health status of the subject based on the detected irregularities.

More specifically, in this embodiment the monitor unit 126 is adapted to classify each of irregularities into one of a plurality of irregularity classifications, and to determine, based on the irregularity classification of each of the irregularities: a value of risk of an adverse event occurrence; and a value of time until care activity requirements change. Thus, it will be appreciated in this example embodiment, wherein the health status of the subject is representative of: a risk of an adverse event occurrence; and a time until care activity requirements change.

In more detail, the monitor unit 126 of this example embodiment classifies each of the irregularities into as an outlier to the trend and/or a changepoint in the trend. Then, if an irregularity is classified as an outlier to the trend, the monitor unit 126 increases a value of risk of an adverse event occurrence. Further, if an irregularity is classified as changepoint in the trend, the monitor unit 126 decreases a value of time until care activity requirements change.

Accordingly, based on detected irregularities and their respective classification (i.e. type), the monitor unit 126 determines a health status of the subject comprising values representative of: a risk of an adverse event occurrence; and a time until care activity requirements change. The determined health status is provided to a prediction unit 128 that is adapted to calculate, based on the determined health status of the subject, an estimated future time at which supervision, care or intervention will be required by the subject. The prediction unit 128 also calculates an estimated future value of a property of at least one of: activity of the subject; and care activity provided to the subject based on the determined trend and the determined health status of the subject. As above, the prediction unit 128 may communicate with one or more data processing resources available in the internet or "cloud" 50. Such data processing resources may undertake part or all of the processing required to estimate future values.

The prediction unit 128 is further adapted to generate an output signal 130 representative of the determined health status of the subject and the future values. In other words, after having analysed irregularities in a trend in a health parameter of the subject (derived from input representative of activity of the subject and/or care activity provided to the subject), an output signal 130 representative of a determined health status of the subject and predicted future values is generated.

The system further comprises a graphical user interface (GUI) 160 for providing information to one or more users. The output signal 130 is provided to the GUI 160 via wired or wireless connection. By way of example, the wireless connection may comprise a short-to-medium-range communicate on link. As indicated in FIG. 1, the output signal 130 is provided to the GUI 160 from system 110. However, where the system, has made use of data processing resources via the internet or cloud 50), an output signal may be made available to the GUI 160 via the internet or cloud 50.

Based on the output signal 130, the GUI 160 is adapted to communicate information by displaying one or more graphical elements in a display area of the GUI 160. In this way, the system may communicate information about a health status (and predicted future values) of the monitored subject that may be useful for indicating that the subject is in need of attention or for estimating when the subject may be expected to require assistance or attention. For example, the GUI 160 may be used to display graphical elements to a medical practitioner, a caregiver, a family member or close relative. Alternatively, or in addition, the GUI 160 may be adapted to display graphical elements to the monitored subject.

Although the embodiment described above employs sensors to detect properties of a fridge door that is manipulated by a monitored subject, it will be understood that many other different properties of a subject and/or object manipulated by the subject may be detected using sensors (of the same or different type) in alternative embodiments. For example, other embodiments may be arranged to: detect a velocity or speed of movement of the subject or the object; detect a magnitude of force applied by the subject to the object; detect a distance travelled by the object or a body part of the subject; detect a rate of acceleration of the object or body part of the subject; detect a reaction time of the subject; and/or detect a bodyweight of the subject.

By way of further example, sleeping behaviour, and the other similar ADLs, can be employed. Sleeping behaviour may be described using a begin and end time of the sleeping, and these times (as well as their duration) can form a statistic that can be monitored over time to vary within bounds. Such bounds can be set manually, but, for example, also determined as once or twice the standard deviation in the values of the statistic (e.g. sleeping duration) over a predetermined time period (e.g. the past month). Another metric can be the number of times the subject leaves their bed during sleeping, and/or their (individual and/or accumulated) duration.

As with sleep, other ADL behaviours can be converted into a statistic that is monitored in a comparable manner. Examples include, time/duration in bathroom, toileting and number of toilet visits per day, leaving house, eating/drinking (kitchen activity), etc.

Figure 2:
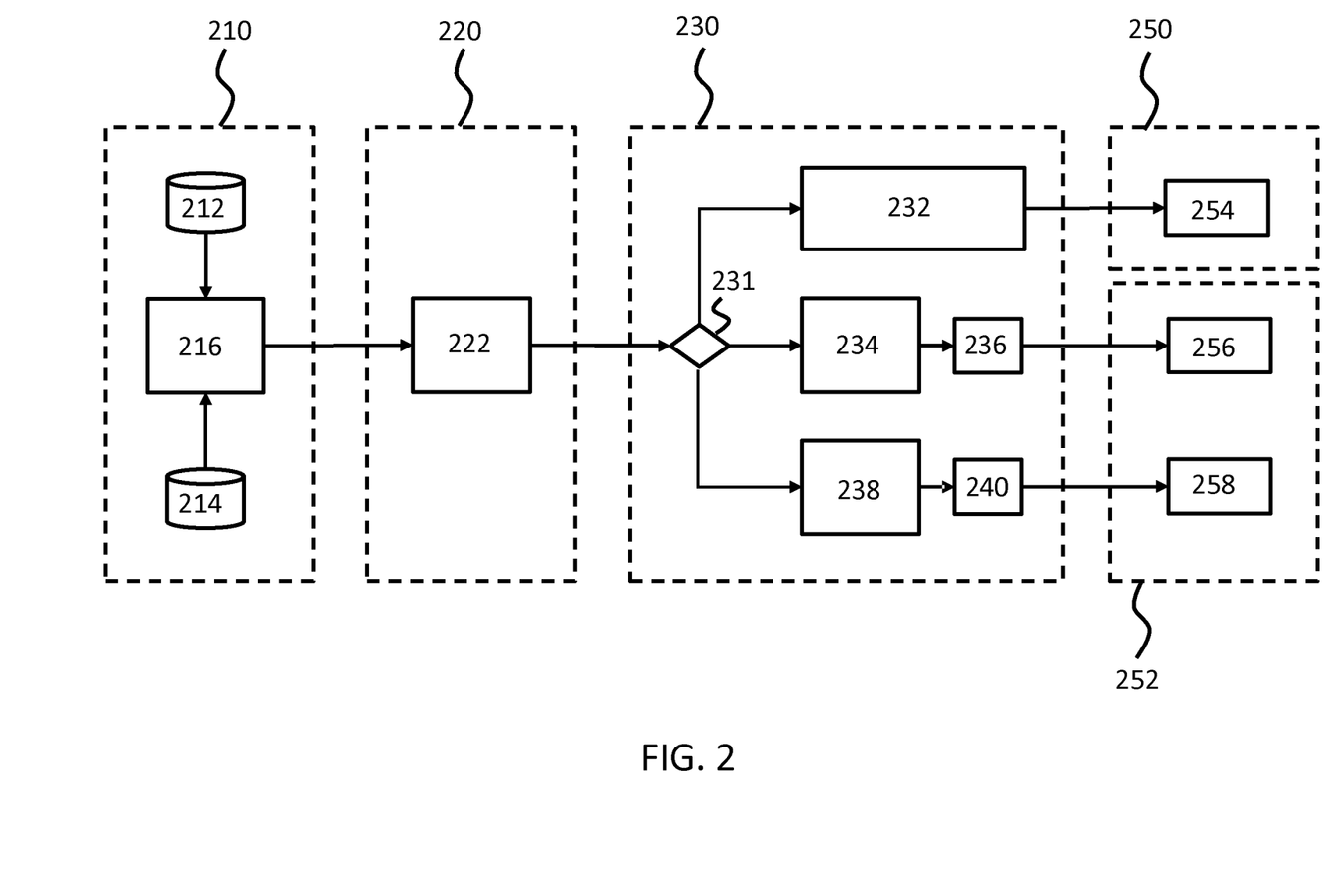
FIG. 2 depicts a flow diagram of a method for monitoring a subject according to an exemplary embodiment.

Referring now to FIG. 2, there is depicted a flow diagram of a method for monitoring a subject according to an exemplary embodiment.

In step 210, a proposed system receives input data. Here, the input data comprises: (i) sensor data 212 comprising information representative of sensed activity of the subject; (ii) care data 214 comprising information representative of care activity provided to the subject.

By way of example, the sensor data 212 may be provided from activity sensors that are mounted in the subject's premises. Such sensors may be adapted to monitor activity and/or behaviour (e.g. walking speed, activity level, sleeping time, wake-up time) of the subject. The care data 214 may be retrieved from one or more databases of the care provider's service system. The care data 214 may, for example, comprise information about care provided to the subject, such as calls, visits, care provision, care types, etc.

The received data 212, 214 is collated in time series 216 of data points which is then provided to the next step of trend analysis 220. In the step 220 of trend analysis, one or more trends 222 in one or more health parameters of the subject are determined based on the received and collated input data 216.

A trend can, for example, be determined from the time series 216 via regression. Next to the trend, a confidence band around it may be determined, e.g. via the standard deviation, possibly after first having removed the trend. Using these data a baseline risk is estimated to encounter an adverse event. In addition, or alternatively, it can be estimated when the next level of care will be needed. This can be in the form of stratification: prediction whether the subject is likely needing a next, increased level of care within a coming time period (e.g. week or month). For example, when the trend is stable (e.g. there is no decline), this need is highly unlikely, and the subject may be concluded to have a health status that is well-suited to a currently received care level. When the trend indicates a decline, a need for a next level of care can be inferred from trends, and their declines, extracted from earlier data on previous patients, for example. Instead of a trend, a highly varying value can also be indicative of a further need for care. Such estimations can be repeated when new data is received into the system.

Next, in step 230, the trend(s) is/are analysed to detect irregularities and any such irregularities are classified into a respective type. Put another way, based on the input data, the system detects and categories anomalies in the data.

As part of 230, the method decides at step 231 whether or not an irregularity has been detected. If no irregularity has been identified, the method moves to step 232 wherein an indication of no irregularities/anomalies is generated. If, however, an irregularity has been identified, it is determined whether the irregularity is an outlier or a changepoint.

By way of example, an outlier to a trend may be defined to be a data event having a current value which deviates more than p-times the standard deviation (e.g. where p=2 or another customizable value) of the trend. Conversely, a changepoint in the trend may be defined as a data event where the trend itself is modified (e.g., faster decline in walking speed or activity level), and such a changepoint may be detected when the last few preceding data points in the time series have a better fit (regression) to a new trend that is different from the previously determined trend for the earlier data points. The point at which the two regression lines split represents the changepoint. Of course, it will be understood that the detection of outliers and changepoints in trends is well-known and that many different methods and approaches for identifying outliers and changepoints are in known in the art (and may thus be employed by proposed embodiments). For example, the known CUmulative SUm control chart (CUSUM) algorithm is an often used algorithm in changepoint detection.

If it is determined that an irregularity is an outlier, the method moves to step 234 wherein the irregularity is classified as an outlier and associated with an incident or adverse event 236. Conversely, if is determined that an irregularity is a changepoint, the method moves to step 238 wherein the irregularity is classified as a changepoint and associated with a change 240 in the trend(s).

Based on the results of the trend analysis of step 230, the method proceeds to the steps of prediction 250 and warning generation 252.

In step 250, a prediction 254 is calculated for a risk of an adverse event occurrence and/or a value of time until care activity requirements change. In this way, there may be predicted an estimated future time at which supervision, care or intervention will be required by the subject.

Also, where an irregularity is classified as an outlier to the trend, a value of risk of an adverse event occurrence is raised in step 256, and a warning potentially generated (depending on the newly-increased risk value). Where an irregularity is classified as a changepoint in the trend, a value of time until care activity requirements change is decreased in step 258 (assuming the trend change is towards the worse), and a warning possibly generated (depending on the newly-decreased time value).

The warning(s) may be conditioned on the fact that a risk was already present in short term, and possibly on other conditions.

By detecting activity of a subject and/or care activity provided to the subject, irregularities in a trend in the detected activity over time may be identified and, from such a trend, a health status of the subject may be monitored. For example, a trend of declining/decreasing force applied by the subject to an object (as detected directly using a pressure sensing pad integrated into an object, such as a door pusher for example, or as detected indirectly using an accelerometer integrated into the object that is moved by the subject) may be used to identify and monitor a trend in the subject's physical strength.

Figure 3:
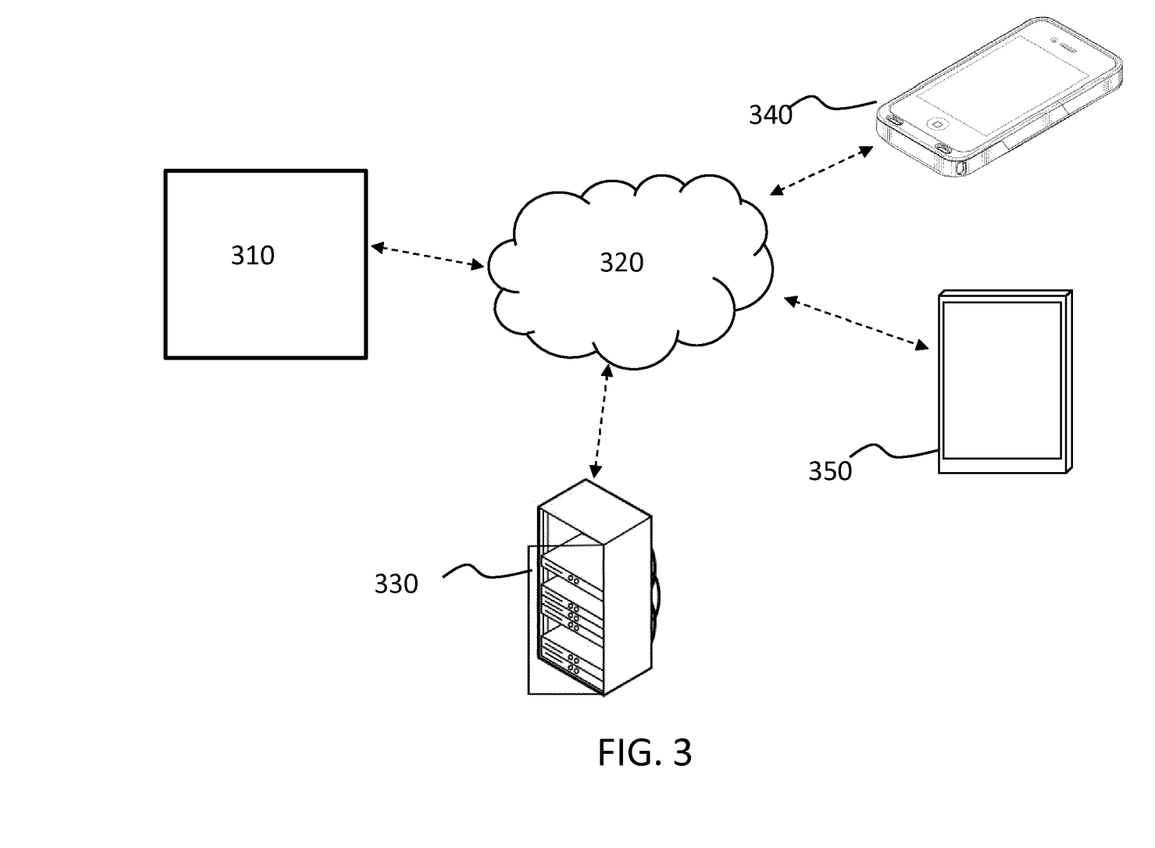
FIG. 3 is a simplified block diagram of a system according to an embodiment.

Referring now to FIG. 3, there is depicted another embodiment of a system according to the invention comprising an activity sensing system 310 adapted to detect activity of the subject. Here, the activity sensing system 310 comprises a high-resolution accelerometer system adapted to be integrated into a device carried or worn by the subject. The activity sensing system 310 is adapted to output one or more signals which are representative of the detected value(s) of a subject's movements.

Although this embodiment has been described as integrating the activity sensing system 310 into a portable device, it will be understood that, in alternative embodiments, the activity sensing system 310 may be provided separately from the subject such that it is installed throughout a monitoring environment for example. Such an alternative arrangement may avoid the need for the subject to carry or wear a device, and thus be less intrusive and/or cheaper. For example, instead of being integrated into a small portable device, the activity sensing system may comprises movement sensors (like Passive Infra-Red sensors and Open-Close sensors) positioned in various rooms so as to detect the subject's presence upon entering and leaving the various rooms.

The activity sensing system 310 communicates the output signals via the internet 320 (using a wired or wireless connection for example) to a remotely located data processing system 330 (such as server). Here, the data processing system comprises a system for monitoring a health status of a subject.

The data processing system 330 is adapted to receive the one or more output signals from the activity sensing system 310 and process, using a processing unit (not shown), the received signal(s) in accordance with an inference/detection algorithm in order to infer/determine a trend in the activity of the subject. More specifically, the algorithm processes the received sensor output signal(s) in combination with historical data relating to one or more previously detected values of the activity of the subject to determine a trend in the subject's movement speed over time.

A trend analysis unit (not shown) of the data processing system 330 then detects irregularities in the determined trend. For example, the trend analysis system identifies whether there are irregularities in the determined trend based on a comparison of the determined trend with a threshold value. Of course, it will be understood that many techniques for identifying irregularities in a trend are widely known, and the trend analysis unit may use any of such method (or combination thereof).

Information about the detected irregularities is passed to a monitor unit (not shown) of the data processing system 330. The monitor unit is adapted to determine a health status of the subject based on the irregularities in the trend. More specifically, the monitor unit classifies each irregularity as either: an outlier to the trend; or a changepoint in the trend. If an irregularity is classified as an outlier to the trend, the monitor unit modifies a value of risk of an adverse event occurrence (e.g. increases the value if the outlier infers an adverse event may be more likely). If an irregularity is classified as a changepoint in the trend, the monitor unit modifies a value of time until care activity requirements change (e.g. decreases the value time if the change in trend represents an acceleration in a deterioration in health status).

Thus, the data processing system 330 provides a centrally accessible processing resource that can receive information from the activity sensing system and run one or more algorithms to transform the received information into an inferred health status of the subject. Information relating to the health status can be stored by the data processing unit (for example, in a database) and provided to other components of the system. Such provision of information about a detected or inferred health status may be undertaken in response to a receiving a request (via the internet 320 for example) and/or may be undertaken without request (i.e. 'pushed').

For the purpose of receiving information about a detected or inferred health status from the data processing system 330, and thus to enable the subject's health to be monitored, the system further comprises first 340 and second 350 mobile computing devices.

Here, the first mobile computing device 340 is a mobile telephone device (such as a smartphone) with a display for displaying graphical elements representative of a subject's health status. The second mobile computing device 350 is a mobile computer such as a Laptop or Tablet computer with a display for displaying graphical elements representative of a subject's detected movement speed.

The data processing system 330 is adapted to communicate output signals to the first 340 and second 350 mobile computing devices via the internet 320 (using a wired or wireless connection for example). As mentioned above, this may be undertaken in response to receiving a request from the first 340 or second 350 mobile computing devices.

Based on the received output signals, the first 340 and second 350 mobile computing devices are adapted to display one or more graphical elements in a display area provided by their respective display. For this purpose, the first 340 and second 350 mobile computing devices each comprise a software application for processing, decrypting and/or interpreting received output signals in order to determine how to display graphical elements. Thus, the first 340 and second 350 mobile computing devices each comprise a processing arrangement adapted to display one or more graphical elements indicating one or more values representative of a health status, and to generate a display control signal for modifying at least one of the size, shape, position, orientation, pulsation or colour of the graphical element based on the one or more values representative of health status.

The system can therefore communicate information about an inferred health status and detected movement speed to users of the first 340 and second 350 mobile computing devices, respectively. For example, each of the first 340 and second 350 mobile computing devices may be used to display graphical elements to a medical practitioner, a caregiver, a family member or close relative.

Figure 4:
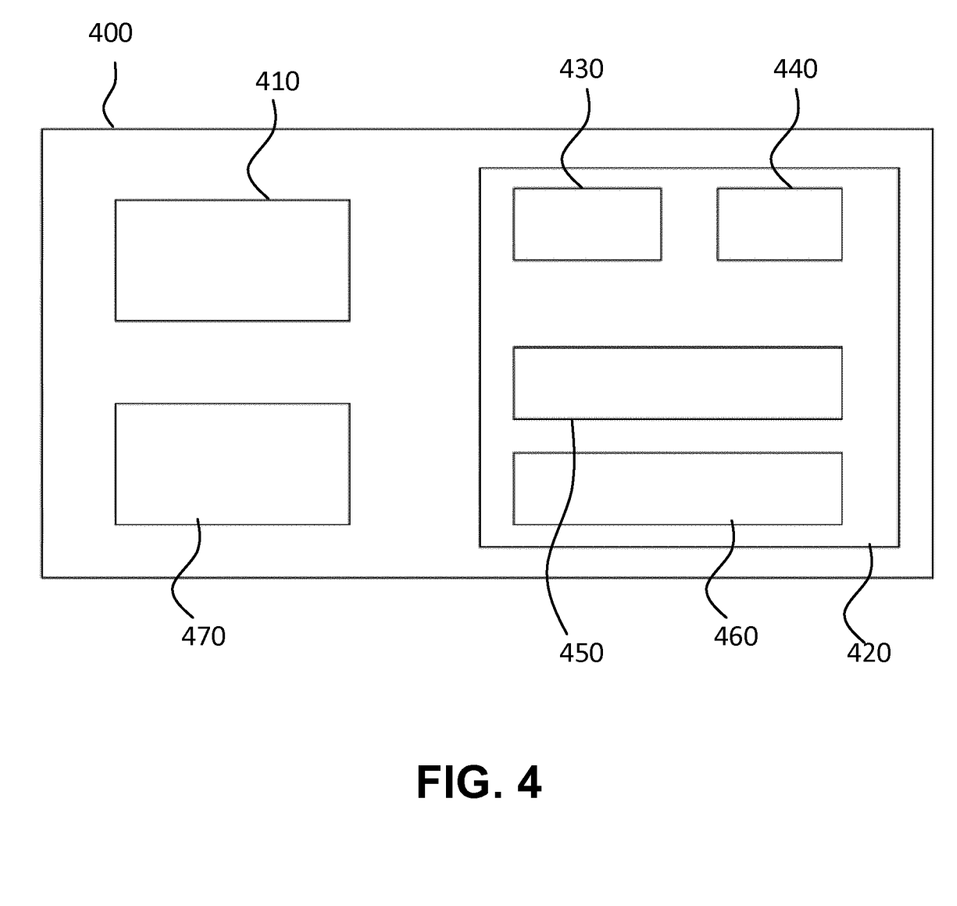
FIG. 4 is a simplified block diagram of a computer within which one or more parts of an embodiment may be employed.

Implementations of the system of FIG. 4 may vary between: (i) a situation where the data processing system 330 communicates display-ready data, which may for example comprise display data including graphical elements (e.g. in JPEG or other image formats) that are simply displayed to a user of a mobile computing device using conventional image or webpage display (which can be web based browser etc.); to (ii) a situation where the data processing system 330 communicates raw data set information that the receiving mobile computing device then processes to determine a trend in movement speed, detect irregularities, determined health status based on the irregularities, and then displays graphical elements based on the determined health status (for example, using local software running on the mobile computing device).

Of course, in other implementations, the processing may be shared between the data processing system 330 and a receiving mobile computing device such that part of the data generated at data processing system 330 is sent to the mobile computing device for further processing by local dedicated software of the mobile computing device. Embodiments may therefore employ server-side processing, client-side processing, or any combination thereof.

Further, where the data processing system 330 does not 'push' information (e.g. output signals), but rather communicates information in response to receiving a request, the user of a device making such a request may be required to confirm or authenticate their identity and/or security credentials in order for the information to be communicated.

FIG. 4 illustrates an example of a computer 400 within which one or more parts of an embodiment may be employed. Various operations discussed above may utilize the capabilities of the computer 400. For example, one or more parts of an ADL monitoring system adapted to monitor a health status of a subject may be incorporated in any element, module, application, and/or component discussed herein.

The computer 400 includes, but is not limited to, PCs, workstations, laptops, PDAs, palm devices, servers, storages, and the like. Generally, in terms of hardware architecture, the computer 400 may include one or more processors 410, memory 420, and one or more I/O devices 470 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 410 is a hardware device for executing software that can be stored in the memory 420. The processor 410 can be virtually any custom made or commercially available processor, a central processing unit (CPU), a digital signal processor (DSP), or an auxiliary processor among several processors associated with the computer 400, and the processor 410 may be a semiconductor based microprocessor (in the form of a microchip) or a microprocessor.

The memory 420 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 420 may incorporate electronic, magnetic, optical, and/or other types of storage media. Note that the memory 420 can have a distributed architecture, where various components are situated remote from one another, but can be accessed by the processor 410.

The software in the memory 420 may include one or more separate programs, each of which comprises an ordered listing of executable instructions for implementing logical functions. The software in the memory 420 includes a suitable operating system (O/S) 450, compiler 440, source code 430, and one or more applications 460 in accordance with exemplary embodiments. As illustrated, the application 460 comprises numerous functional components for implementing the features and operations of the exemplary embodiments. The application 460 of the computer 400 may represent various applications, computational units, logic, functional units, processes, operations, virtual entities, and/or modules in accordance with exemplary embodiments, but the application 460 is not meant to be a limitation.

The operating system 450 controls the execution of other computer programs, and provides scheduling, input-output control, file and data management, memory management, and communication control and related services. It is contemplated by the inventors that the application 460 for implementing exemplary embodiments may be applicable on all commercially available operating systems.

Application 460 may be a source program, executable program (object code), script, or any other entity comprising a set of instructions to be performed. When a source program, then the program is usually translated via a compiler (such as the compiler 440), assembler, interpreter, or the like, which may or may not be included within the memory 420, so as to operate properly in connection with the O/S 450. Furthermore, the application 460 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, Python, ADA, .NET, and the like.

The I/O devices 470 may include input devices such as, for example but not limited to, a mouse, keyboard, scanner, microphone, camera, etc. Furthermore, the I/O devices 470 may also include output devices, for example but not limited to a printer, display, etc. Finally, the I/O devices 470 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 470 also include components for communicating over various networks, such as the Internet or intranet.

If the computer 400 is a PC, workstation, intelligent device or the like, the software in the memory 420 may further include a basic input output system (BIOS) (omitted for simplicity). The BIOS is a set of essential software routines that initialize and test hardware at startup, start the O/S 450, and support the transfer of data among the hardware devices. The BIOS is stored in some type of read-only-memory, such as ROM, PROM, EPROM, EEPROM or the like, so that the BIOS can be executed when the computer 400 is activated.

When the computer 400 is in operation, the processor 410 is configured to execute software stored within the memory 420, to communicate data to and from the memory 420, and to generally control operations of the computer 400 pursuant to the software. The application 460 and the O/S 450 are read, in whole or in part, by the processor 410, perhaps buffered within the processor 410, and then executed.

When the application 460 is implemented in software it should be noted that the application 460 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 460 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to subjectalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A system for monitoring a health status of a subject, wherein the system comprises:
 a signal interface adapted to receive input data relating to a plurality of event occurrences for the subject, the input data comprising, for each event occurrence, information representative of at least one of activity of the subject and care activity provided to the subject;
 a processor adapted to determine a trend in a health parameter of the subject based on the input data;
 a trend analyzer adapted to detect one or more irregularities in the determined trend; and
 a monitor adapted to classify each of the one or more irregularities as at least one of an outlier to the determined trend and a changepoint in the determined trend and to determine the health status of the subject based on the irregularity classification of each of the one or more irregularities,
 wherein the health status of the subject is representative of at least one of a risk of an adverse event occurrence and a time until care activity requirements change, and
 wherein the monitor is adapted to determine, based on the irregularity classification of each of the one or more irregularities, at least one of a value of the risk of the adverse event occurrence and a value of the time until care activity requirements change, and
 wherein the changepoint is determined when last data points of the determined trend are a better fit to a new trend which is different from the determined trend.

2. The system of claim 1, wherein the trend analyzer is adapted to identify whether there are one or more irregularities in the determined trend based on at least one of a comparison of the determined trend with a threshold value a comparison of information of an event occurrence with an average value and a comparison of the determined trend with a predetermined trend.

3. The system of claim 2, wherein the threshold value is determined based on at least one of:
 one or more previously obtained values of a property of at least one of an activity of the subject and care activity provided to the subject; and
 one or more previously determined changes in values of a property of at least one of an activity of the subject and care activity provided to the subject.

4. The system of claim 1, further comprising:
 a predictor adapted to calculate, based on the determined health status of the subject, an estimated future time at which supervision, care or intervention will be required by the subject.

5. The system of claim 4, wherein the predicter is further adapted to calculate an estimated future value of a property of at least one of activity of the subject and care activity provided to the subject based on the determined trend and the determined health status of the subject.

6. The system of claim 1, wherein the information representative of at least one of activity of the subject and care activity provided to the subject comprises information relating to a detected value of a property of at least one of the subject and an object manipulated by the subject.

7. The system of claim 6, wherein the property comprises at least one of:
 a velocity of movement of the subject or the object;
 a measure of force applied by the subject to the object;
 a distance travelled by the object or a body part of the subject;
 a rate of acceleration of the object or body part of the subject;
 a measure of posture of the subject;
 a reaction time of the subject;
 a measure of posture of the subject; and
 a bodyweight of the subject.

8. The system of claim 1 further comprising a sensor adapted to be coupled to the subject or an object, wherein the sensor comprises at least one of a weight sensor configured to detect a bodyweight of the subject, a pressure sensor configured to directly measure a force applied by the subject to an object, and a timer configured to detect an amount of elapsed time between a prompt provided to the subject and a response to the prompt from the subject.

9. The system of claim 1, wherein the outlier is associated with event occurrences, and wherein the changepoint is indicative of a point where the determined trend is modified.

10. The system of claim 1, wherein the outlier is associated with a number of event occurrences, and wherein the changepoint is indicative of a new trend which is different from the determined trend.

11. The system of claim 1, wherein the monitor is configured to increase the value of the risk in response to classification of the irregularity as the outlier to the determined trend, and to decrease the value of the time in response to classification of the irregularity as the changepoint in the determined trend.

12. The system of claim 1, wherein the outlier is determined when the value of the risk of the adverse event occurrence deviates more than p times a standard deviation of the value over a predetermined time period, where the p is an integer.

13. The system of claim 1, further comprising a location sensor worn by the subject and a weight sensor configured to detect a bodyweight of the subject, wherein data from the location sensor is used to confirm that a weight reading taken by the weight sensor is attributable to the subject.

14. A method for monitoring a subject, wherein the method comprises acts of:
- receiving, at a signal interface of a system for monitoring a health status of the subject, input data relating to a plurality of event occurrences for the subject, the input data comprising, for each event occurrence, information representative of at least one of activity of the subject and care activity provided to the subject;
- determining, with a processor of the system, a trend in a health parameter of the subject based on the input data;
- detecting, with a trend analyzer of the system, one or more irregularities in the trend;
- classifying, with a monitor of the system, each of the one or more irregularities as at least one of an outlier to the trend and a changepoint in the trend; and
- determining, with the monitor of the system, a health status of the subject based on the irregularity classification of each of the one or more irregularities,
- wherein the health status of the subject is representative of at least one of a risk of an adverse event occurrence and a time until care activity requirements change,
- wherein the act of determining a health status of the subject comprises:
- determining, based on the irregularity classification of each of the one or more irregularities, at least one of a value of the risk of an adverse event occurrence and a value of the time until care activity requirements change, and
- wherein the changepoint is determined when last data points of the determined trend are a better fit to a new trend which is different from the determined trend.

15. The method of claim 14, wherein the detecting act identifies whether there are one or more irregularities in the determined trend based on at least one of a comparison of the determined trend with a threshold value a comparison of information of an event occurrence with an average value and a comparison of the determined trend with a predetermined trend.

16. The method of claim 14, further comprising an act of calculating, by a predicter based on the determined health status of the subject, an estimated future time at which supervision, care or intervention will be required by the subject.

17. The method of claim 14, wherein the information representative of at least one of activity of the subject and care activity provided to the subject comprises information relating to a detected value of a property of at least one of the subject and an object manipulated by the subject.

18. The method of claim 14, further comprising acts of:
- determining location of the subject by a location sensor worn by the subject;
- determining a bodyweight of the subject by a weight sensor; and
- confirming that a weight reading taken by the weight sensor is attributable to the subject using data from the location sensor.

19. A non-transitory computer program product for monitoring a subject, wherein the computer program product comprises computer-readable program code executable to perform acts of:
- receiving, at a signal interface of a system for monitoring a health status of the subject, input data relating to a plurality of event occurrences for the subject, the input data comprising, for each event occurrence, information representative of at least one of activity of the subject and care activity provided to the subject;
- determining, with a processor of the system, a trend in a health parameter of the subject based on the input data;
- detecting, with a trend analyzer of the system, one or more irregularities in the trend;
- classifying, with a monitor of the system, each of the one or more irregularities as at least one of an outlier to the trend and a changepoint in the trend; and
- determining, with the monitor of the system, a health status of the subject based on the irregularity classification of each of the one or more irregularities,
- wherein the health status of the subject is representative of at least one of a risk of an adverse event occurrence and a time until care activity requirements change,
- wherein the act of determining a health status of the subject comprises:
- determining, based on the irregularity classification of each of the one or more irregularities, at least one of a value of the risk of an adverse event occurrence and a value of the time until care activity requirements change, and
- wherein the changepoint is determined when last data points of the determined trend are a better fit to a new trend which is different from the determined trend.

* * * * *